(12) United States Patent
Vanderpool et al.

(10) Patent No.: US 12,414,773 B2
(45) Date of Patent: *Sep. 16, 2025

(54) SYSTEM AND METHOD FOR BLOCKING A LUMINAL BODY

(71) Applicant: Invertes Inc., Torrance, CA (US)

(72) Inventors: Charles H. Vanderpool, Central Point, OR (US); Scott Tarvyd MacDonald, Torrance, CA (US); Aiguo Wu, Woodbridge, VA (US)

(73) Assignee: Invertes Inc., Torrance, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/088,542

(22) Filed: Mar. 24, 2025

(65) Prior Publication Data
US 2025/0221713 A1 Jul. 10, 2025

Related U.S. Application Data

(63) Continuation of application No. 18/981,354, filed on Dec. 13, 2024.
(Continued)

(51) Int. Cl.
A61B 17/00 (2006.01)
A61B 17/12 (2006.01)

(52) U.S. Cl.
CPC .... *A61B 17/12031* (2013.01); *A61B 17/0057* (2013.01); *A61B 2017/00584* (2013.01)

(58) Field of Classification Search
CPC ............ A61B 17/1114; A61B 17/1155; A61B 17/115; A61B 2017/1142; A61B 1/31; A61B 17/00234; A61B 17/320016; A61B 2017/306; A61B 2017/00557; A61B 2017/3452; A61B 1/00147; A61B 1/0055; A61B 1/0058; A61B 1/008; A61B 1/05; A61B 17/0293; A61B 17/068; A61B 17/0686; A61B 17/11; A61B 17/1152; A61B 17/1285; A61B 17/32053; A61B 18/14; A61B 2017/00115; A61B 2017/00287; A61B 2017/00296; A61B 2017/003; A61B 2017/00314;
(Continued)

(56) References Cited

U.S. PATENT DOCUMENTS 5,839,639 A 11/1998 Sauer et al.
6,083,241 A 7/2000 Longo et al.
(Continued)

FOREIGN PATENT DOCUMENTS

WO 1991002491 3/1991

*Primary Examiner* — Jon Eric C Morales
(74) *Attorney, Agent, or Firm* — Eric Karich; Karich & Associates

(57) ABSTRACT

A surgical system for blocking a luminal body at a selected location has a tubular body that extends from a proximal end to a distal end, and a blocking device on the distal end of the tubular body. The blocking device has a guide cap and a gripping feature, and at least one annular inflatable portion positioned around an outer circumference of the gripping feature. A first conduit through the tubular body is connected to a pressure source for inflating the annular inflatable portion, and a second conduit through the tubular body is connected to a vacuum source for suctioning a luminal wall of the luminal body against the gripping feature.

9 Claims, 7 Drawing Sheets

Related U.S. Application Data

(60) Provisional application No. 63/609,856, filed on Dec. 13, 2023.

(58) Field of Classification Search
CPC ........... A61B 2017/00323; A61B 2017/00349; A61B 2017/00353; A61B 2017/00734; A61B 2017/00867; A61B 2017/07257; A61B 2017/07264; A61B 2017/07285; A61B 2017/1103; A61B 2017/111; A61B 2017/1125; A61B 2017/1132; A61B 2017/22034; A61B 2017/22054; A61B 2017/2925; A61B 2034/2059; A61B 1/005; A61B 2017/00818
See application file for complete search history.

(56) References Cited

U.S. PATENT DOCUMENTS

| | | |
|---|---|---|
| 6,117,148 A | 9/2000 | Ravo et al. |
| 7,141,055 B2 | 11/2006 | Abrams et al. |
| 7,210,609 B2 | 5/2007 | Leiboff et al. |
| 8,361,090 B2 | 1/2013 | Belson |
| 11,559,293 B1 | 1/2023 | Vanderpool |
| 2012/0024935 A1 | 2/2012 | Shelton |
| 2022/0061863 A1* | 3/2022 | Lorenzo ............... A61M 25/01 |

* cited by examiner

SYSTEM AND METHOD FOR BLOCKING A LUMINAL BODY

CROSS-REFERENCE TO RELATED APPLICATIONS

This application for a utility patent is a continuation of a previously filed utility patent, now pending, having the application Ser. No. 18/981,354, filed Dec. 13, 2024, which claims the benefit of U.S. Provisional Application No. 63/609,856, filed Dec. 13, 2023.

BACKGROUND OF THE INVENTION

Field of the Invention

This invention relates generally to surgical systems and methods, and more particularly to a surgical system that includes a blocking device for blocking a luminal body such as a blood vessel or similar tubular body structure.

Description of Related Art

There is a need in the medical field to block a luminal body, such as a blood vessel or similar tubular body structure, in this embodiment for blocking blood flow during a surgery. In one embodiment, the blocking device may be used to block the aorta of a person or animal, for treating an aortic aneurysm (AA), although this example is illustrative and not limiting, and the invention may be used in a similar fashion for a wide variety of uses.

An AA is characterized by permanent full-thickness dilation of the aortic wall, greater than 50% in diameter of normal size, and it can be generally classified into thoracic aortic aneurysm (TAA), abdominal aortic aneurysm (AAA), or other forms, according to the involved segments. Although most AAs are asymptomatic at the time of diagnosis, the incidence of complications increases as the aneurysm expands. The complications of AA, dissection and rupture, are usually catastrophic, with an almost 100% mortality rate. For elective AAA repair, the 28-day mortality rate was reported to be 3.3%-27.1% in men and 3.8%-54.3% in women in a Dutch population. In China, the overall 30-day mortality of infrarenal AAA repair was approximately 8.8% in a single vascular center.

In an investigation of the general American population, the AAA-related mortality rate was 2.2 deaths per 100,000 in 2016. AA is one of the major cardiovascular diseases with an increased number of years of life lost (YLLs) and deaths globally.

Treatment is typically accomplished via open heart surgery wherein the chest is opened, the heart is stopped, and then the damaged part of the aorta is replaced with a graft. This process is obviously extremely difficult to perform given the time constraints in stopping the heart, as well as traumatic to the patient, and often leads to fatal outcomes.

There is a need in the art for an alternative method of treatment that does not involve stopping the heart of the patient to make this repair. The present invention fulfills these needs and provides further advantages as described in the following summary.

SUMMARY OF THE INVENTION

The present invention teaches certain benefits in construction and use which give rise to the objectives described below.

The present invention provides a surgical system for blocking a luminal body at a selected location. The surgical system comprises a tubular body that extends from a proximal end to a distal end, and a blocking device on the distal end of the tubular body. The blocking device has a guide cap and a gripping feature, and at least one annular inflatable portion positioned around an outer circumference of the gripping feature. A first conduit through the tubular body is connected to a pressure source for inflating the annular inflatable portion, and a second conduit through the tubular body is connected to a vacuum source for suctioning a luminal wall of the luminal body against the gripping feature. Additional conduits may be provided for other purposes, such as allowing fluid repositioning, as discussed below.

A primary objective of the present invention is to provide a surgical system having advantages not taught by the prior art.

Another objective is to provide a surgical system that allows an aorta to be blocked for a repair procedure without the need to stop the heart of the patient.

A further objective is to provide a surgical system having a blocking device that can be inserted through an incision and then inflated to grip a luminal wall and block a luminal body.

Other features and advantages of the present invention will become apparent from the following more detailed description, taken in conjunction with the accompanying drawings, which illustrate, by way of example, the principles of the invention.

BRIEF DESCRIPTION OF THE DRAWINGS

The accompanying drawings illustrate the present invention.

DETAILED DESCRIPTION OF THE INVENTION

The above-described drawing figures illustrate the invention, a blocking device used to perform a surgical procedure within a luminal body of a person or other animal. In the present embodiment, the device is illustrated being used for repairing an aortic aneurysm in a human; however, those skilled in the art may use this device in any luminal body for a wide range of surgical procedures.

Figure 1:
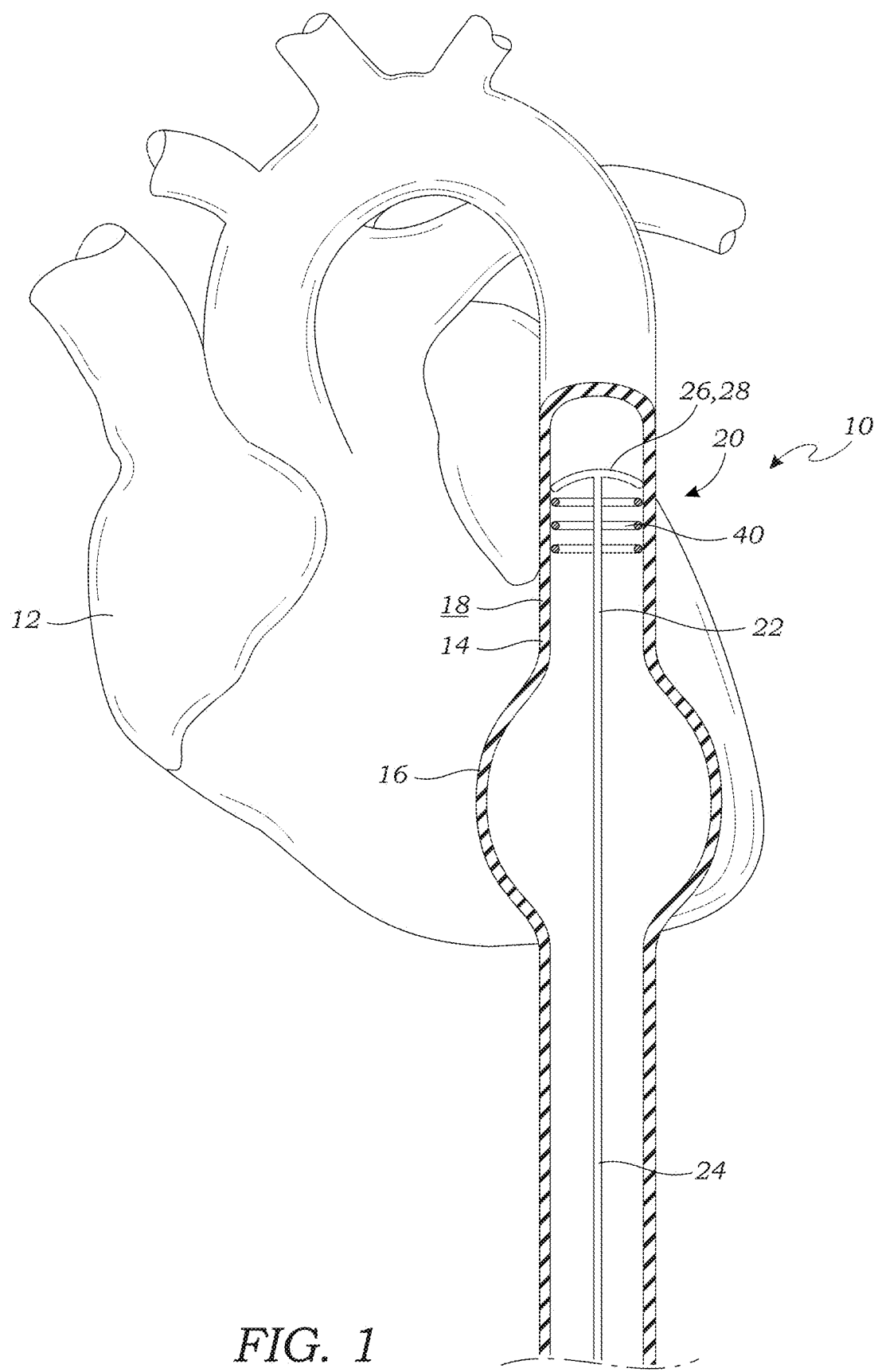
FIG. 1 illustrates a blocking device for blocking a luminal body, in this embodiment part of a surgical system for repairing an aortic aneurysm according to one embodiment of the present invention, illustrating the blocking device being positioned in an aorta of a heart upstream from an aneurism, to block fluid flow through the aorta.

FIG. 1 illustrates one embodiment of a blocking device 20 for blocking a luminal body 14, in this embodiment part of a surgical system 10 for repairing an aortic aneurysm 16 according to one embodiment of the present invention. FIG. 1 illustrates the blocking device 20 being positioned in an aorta of a heart 12 upstream from an aneurism, to block fluid flow through the aorta. The blocking device 20 may be used in any artery or vein, or any other luminal body.

The system of FIG. 1 includes the blocking device 20 shown inside of the luminal body 14 that has the aneurysm 16. The blocking device 20 is adapted to be inserted into the luminal body 14 through an incision (not shown) to treat the aneurysm 16 by temporarily blocking the aorta so that the aneurysm 16 may be repaired, without requiring the heart 12 to be stopped. Since the heart remains beating and supplying blood to the brain, the surgery may last up to 20 minutes, making the process much easier for the surgeon, and less traumatic to the patient, resulting in much better outcomes.

The repair procedure may involve a resecting of the tissue, the placement of a stent (not shown) or other suitable device inside the aneurysm 16, or any other similar or equivalent surgical procedure known in the art. While one particular embodiment is discussed, in other embodiments, the blocking device 20 may be used to operate on other luminal bodies, such as for other vascular problems, tumor removal, embolisms, and the like, in arteries, veins, abdominal cavities, or other part of the body that could benefit from the present invention as-described, and any similar or equivalent procedures should be considered within the scope of the present invention.

Figure 2:
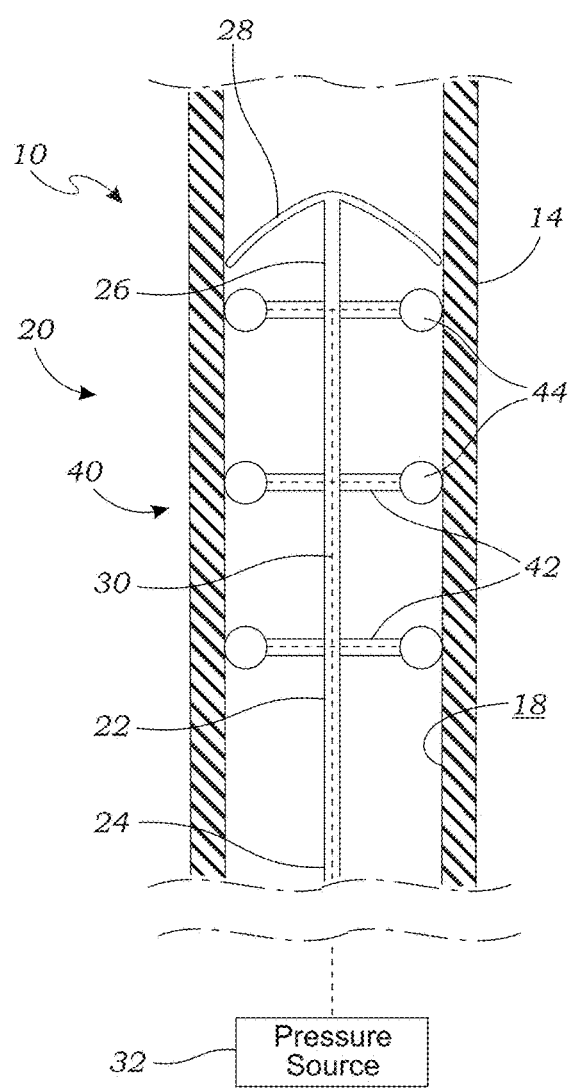
FIG. 2 is an up-close view of the blocking device inserted into the aorta so that gripping features are positioned within the aorta in a deflated state.
Figure 3:
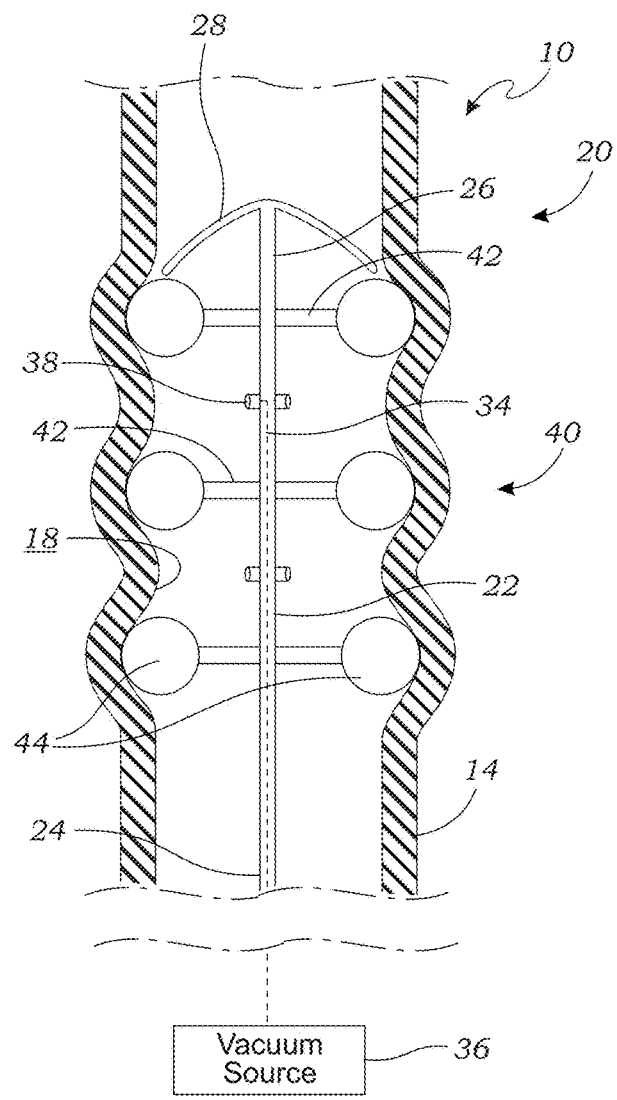
FIG. 3 is an up-close view of the blocking device once the gripping features have been inflated to an inflated state.

FIG. 2 is an up-close view of the blocking device 20 inserted into the aorta so that gripping features 40 are positioned within the aorta in a deflated state. FIG. 3 is an up-close view of the blocking device 20 once the gripping feature 40 has been inflated to an inflated state. As shown in FIGS. 1-3, the surgical system comprises a tubular body 22 that extends from a proximal end 24 to a distal end 26, and the blocking device 20 on the distal end 26 of the tubular body 22. The tubular body 22 is sized and shaped to be inserted into the aorta through an incision(s), and fed through a blood vessel to the aneurysm 16, where the blocking device 20 may be positioned past and adjacent the aneurysm 16 to block the aorta for repair. For purposes of this application, the term "adjacent" is defined to mean a suitable distance for performing the operation described below, as determined by the physician. Several embodiments of the gripping feature 40 are discussed in the following Figure descriptions. The blocking device 20 has a guide cap 28 at the distal end 26, and the gripping feature 40 has at least one annular inflatable portion 44 around an outer circumference of the gripping feature 40. In this embodiment, the guide cap 28 has a conical or an arcuate shape, but any suitable shape or structure known in the art may be used.

The gripping feature 40 is adapted for establishing a firm gripping connection with an inner surface 18 of the luminal body 14, for anchoring the device in place. In this embodiment, the gripping feature includes at least one annular plug 42 that extends radially from the tubular body 22 and terminates in the inflatable portion 44. The annular plugs 42 and annular inflatable portions 44 are concentrically aligned around the axis of the tubular body 22, best shown in FIG. 6. In the embodiment of FIGS. 2-3, the annular inflatable portions 44 each have a symmetrical tubular shape, but other shapes and structures may be constructed, other examples being shown in FIGS. 4-9 and discussed below. While three inflatable portions 44 are illustrated, any suitable number may be included, including one, which should be considered within the scope of the present invention.

As illustrated in FIG. 2, a first conduit 30 extends through the tubular body 22 and is connected to a pressure source 32 for inflating the annular inflatable portion 44. In this embodiment, the first conduit 30 passes up the tubular body 22 and through the annular plugs 42 to access the annular inflatable portions 44. As shown in FIG. 3, a second conduit 34 extends through the tubular body 22 and is connected to a vacuum source 36, i.e., a source of lower pressure which is lower than atmospheric pressure, for suctioning a luminal wall of the luminal body 14 against the gripping feature 40, discussed in greater detail below. In this embodiment, the tubular body 22 includes a plurality of valves 38 positioned between each annular plug 42 so that the inner surface 18 of the luminal body 14 may be suctioned to the blocking device 20, thereby effectively blocking the aneurysm 16 from, for example, the passage of fluids from upstream. In some embodiments, the valves 38 may be closeable, so that once suctioned, the vacuum may be shut off without losing the achieved blocking function. Furthermore, there may be some form of closable valve (not shown) of the first conduit 30, so that the pressure source 32 may cease its input without losing inflation of the inflatable portions 44. In further embodiments, the pressure source 32 and the vacuum source 36 may be separate structures, or they may be integrated into a single structure/device.

Figure 4:
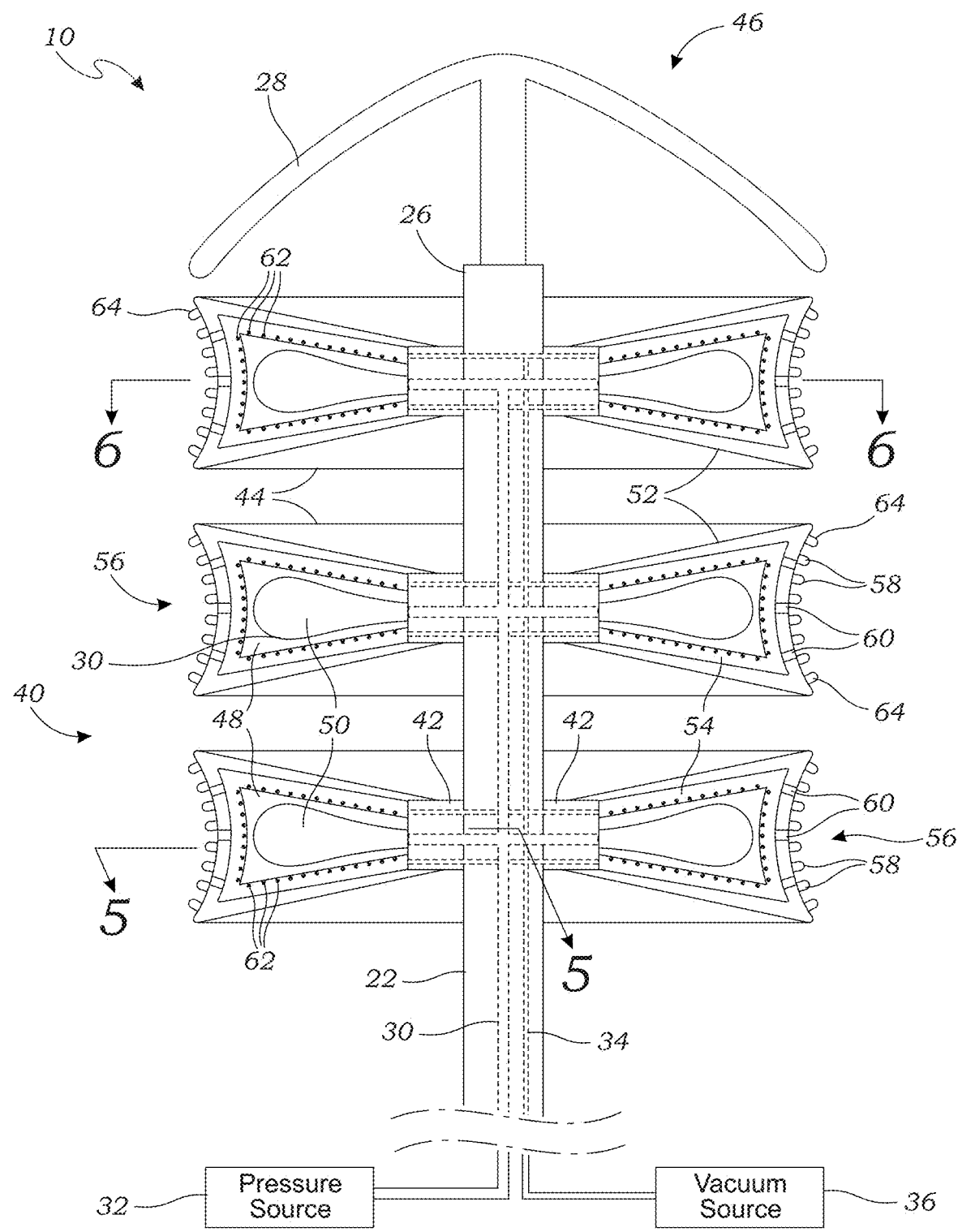
FIG. 4 is a side elevation cross-sectional view of a second embodiment of the blocking device, illustrating the gripping features in a partially inflated state.
Figure 5:
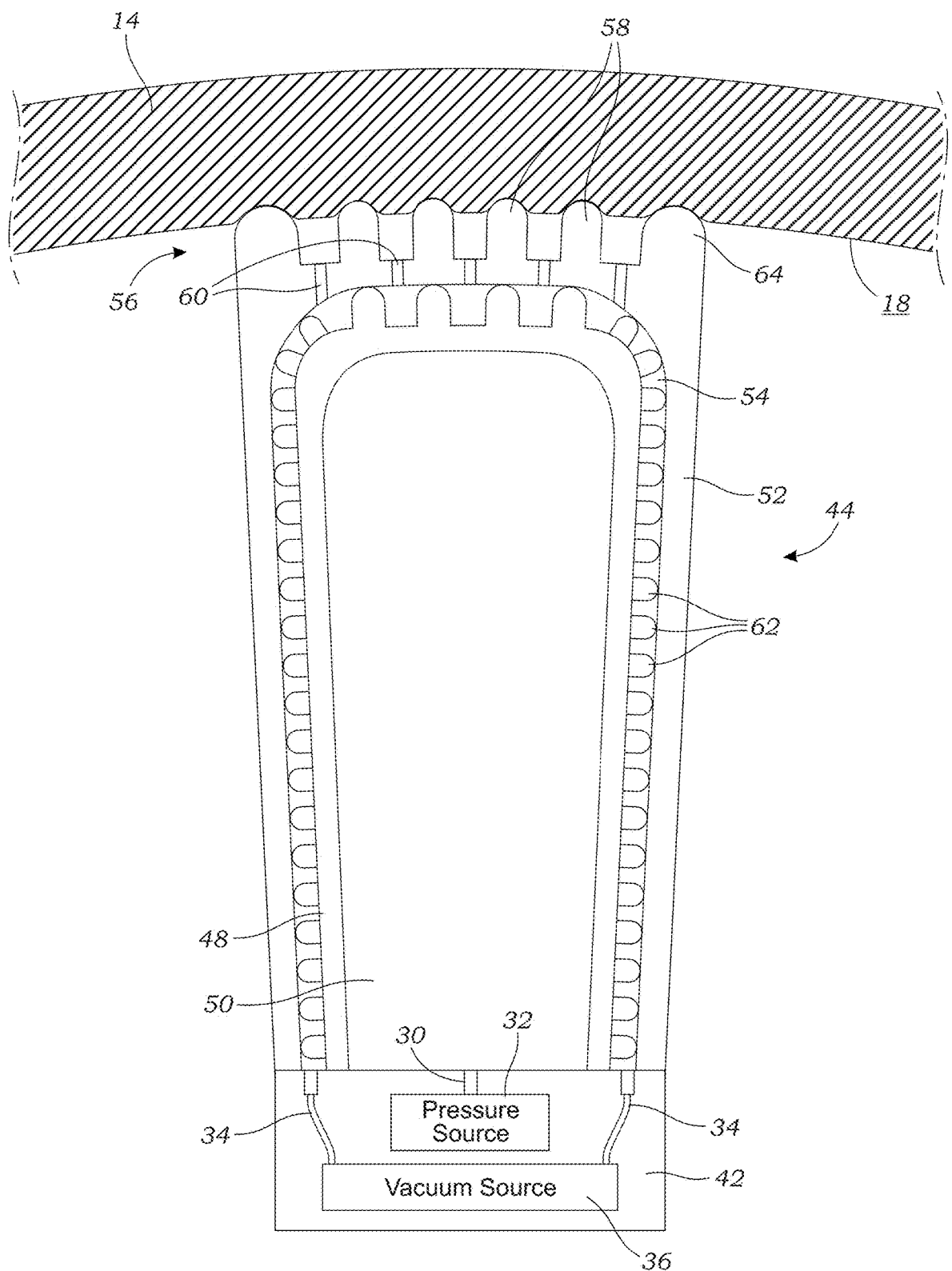
FIG. 5 is a cross-sectional view taken along lines 5-5 in FIG. 4, illustrating the gripping feature in an inflated state.

FIG. 4 is a side elevation cross-sectional view of a second embodiment of the blocking device 20, illustrating the gripping feature 40 in a deflated state, and FIG. 5 is a cross-sectional view taken along lines 5-5 in FIG. 4, illustrating the gripping feature 40 in an inflated state. As shown in FIGS. 4-5, in this embodiment, the inflatable portions 44 each include an inner layer 48 forming an inner body 50, and an outer layer 52 forming an outer body 54, which may be recessed in a concave shape in the deflated state, and expanded so that the outer layer 52 contacts the inner surface 18 of the luminal body 14 in an inflated state.

Each outer layer 52 may include a clamping area 56 around the outer periphery that includes a "tread" 58, in this embodiment being in the form of a plurality of posts 58, wherein a plurality of holes 60 may be formed between the posts 58 on the clamping area 56. While posts are illustrated and described, any form of tread may be constructed, e.g., ridges, waves, cones, etc. The tread 58 may be formed of a pliable material (e.g., rubber, etc.). Furthermore, each inner layer 48 may include a plurality of spacers 62 around the entire outside of the inner layer 48, in this embodiment also being in the form of a plurality of posts.

As illustrated, in this embodiment, the second conduit 34 extends into the inflatable portion(s) 44, rather than between the inflatable portions 44, for suctioning the clamping area 56 against the inner surface 18 of the luminal body 14. The first conduit 30 communicates with the inner body 50, and the second conduit 34 communicates with the outer body 54, outside of the inner body 50. In this manner, pressure may be applied to the inner body 50 to inflate it, which presses the clamping area 56 of the outer layer 52 against the luminal body 14. The plurality of spacers 62 maintain a separation between the inner and outer layers 48 and 52, so that vacuum may then be introduced between the inner and outer layers 48 and 52 to suction the clamping area 56 against the luminal body 14. The inner layer 48 does not include holes, allowing air to pass between the inner and outer layers 48 and 52, while maintaining pressure of the inner body 50. As shown in FIG. 5, in some embodiments, side ridges 64 may be formed on outer edges of the clamping area 56 to seal the area between the clamping area 56 and the luminal body 14 to contain the vacuum force. In this embodiment, the holes 60 are formed in a "zig-zag" configuration across the clamping area 56, but the holes 60 could potentially be formed in any suitable configuration, as determined by one skilled in the art.

Figure 6:
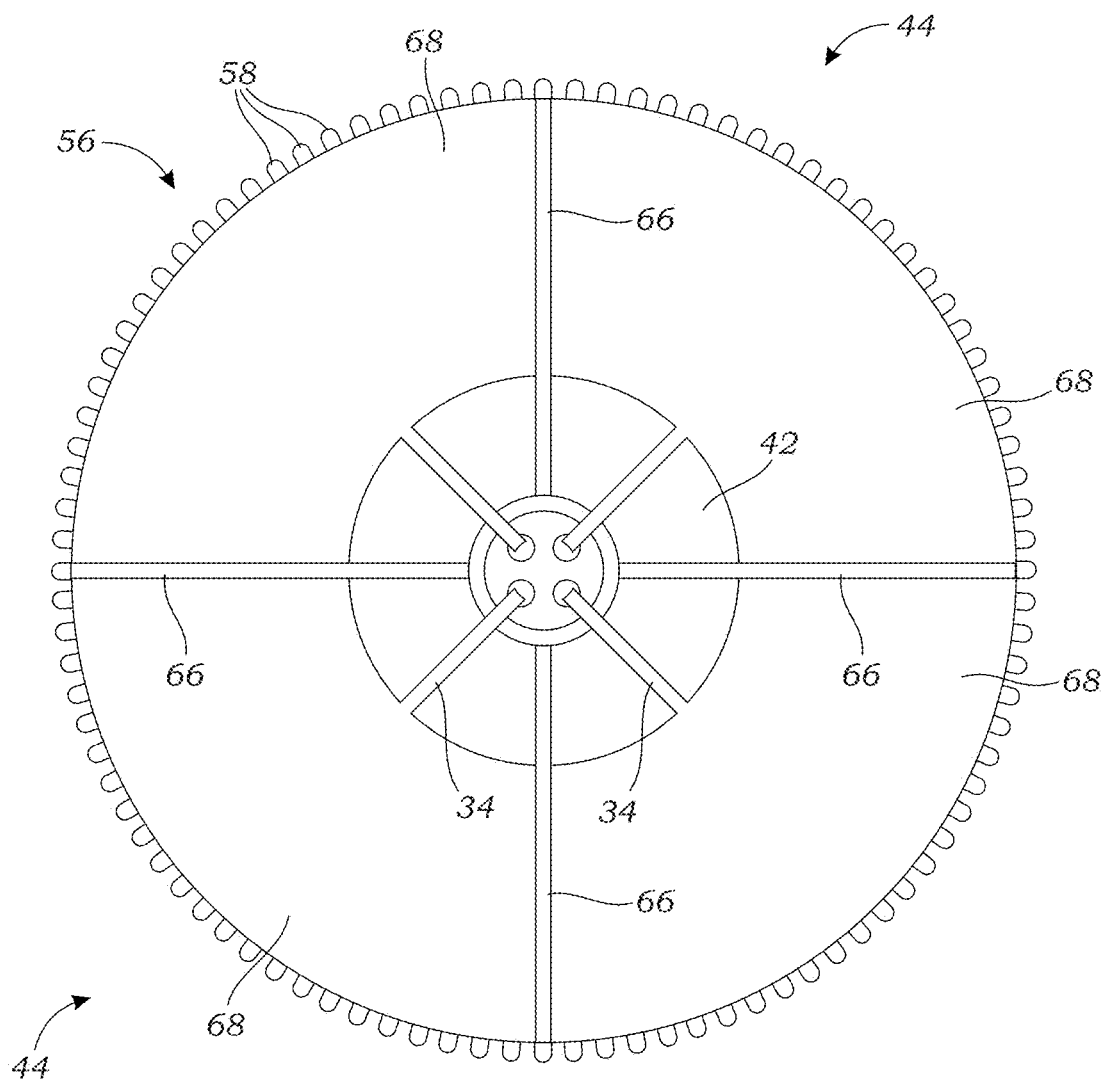
FIG. 6 is a cross-sectional view taken along lines 6-6 in FIG. 4, illustrating dividing walls circumferentially spaced to divide an inflatable portion of the gripping feature into a plurality of chambers.

FIG. 6 is a cross-sectional view of the blocking device 20 taken along lines 6-6 in FIG. 4, illustrating dividing walls 66 circumferentially spaced to divide each of the inflatable portions 44 into a plurality of chambers 68. As shown in FIG. 6, the dividing walls 66 may extend radially from the tubular body 22 of the blocking device 20, dividing the annular plug 42 and the annular inflatable portion 44 into quadrants. While quadrants are illustrated, any suitable number of chambers 68 may be implemented for the purpose described below. In this embodiment, the first and second conduits 30 and 34 are also split into the same number of valves as there are chambers 68, for inflating and vacuuming each chamber 68 as needed. In FIG. 6, the holes 60 for suctioning are not visible, but this is only for the purpose of clarity.

In a typical use where the blocking device 20 inserted, there may be excess fluid such as blood seeping/flowing from a portion of the inner surface 18 of the luminal body 14, i.e., if there is a lesion in the inner surface 18, or similar. To prevent the vacuum continuously aspirating the fluid into the entire inflatable portion 44 and thereby preventing proper clamping of the clamping surface, only one of the chambers 68 may instead be prevented from clamping, wherein the remaining chambers 68 can clamp sufficiently to allow the luminal body 14 to be blocked for a surgical procedure. In some cases, the valve of the second conduit 34 (connected to the vacuum source 36) may be closed off in the affected chamber, so fluid is not drawn from that chamber. In cases where there is a plurality of tiered inflatable portions, a single chamber of one of the inflatable portions 44 failing to suction will not pose an issue for the procedure.

Figure 7:
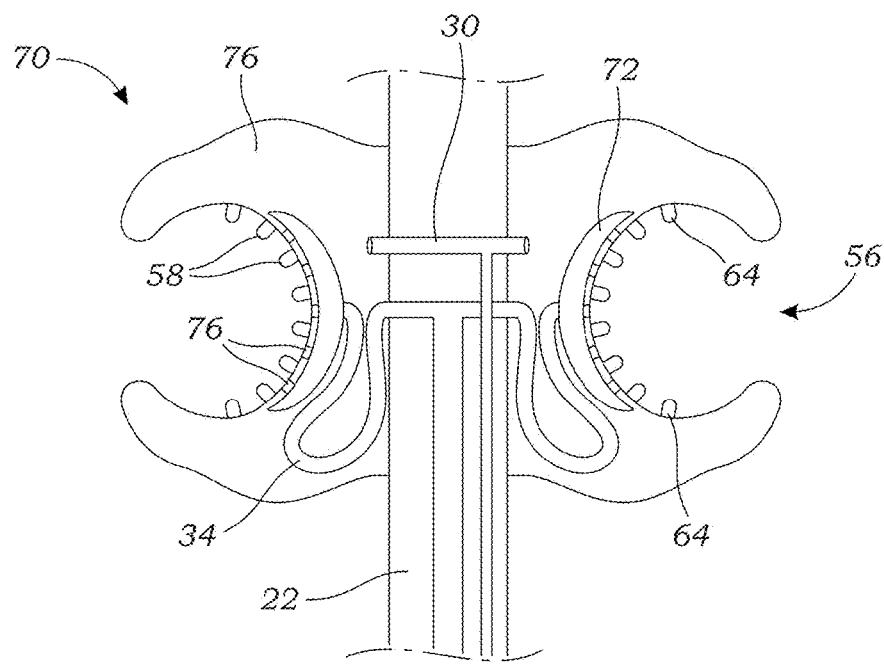
FIG. 7 is a side cross section of another embodiment of a gripping feature, illustrating the gripping feature in a deflated state.
Figure 8:
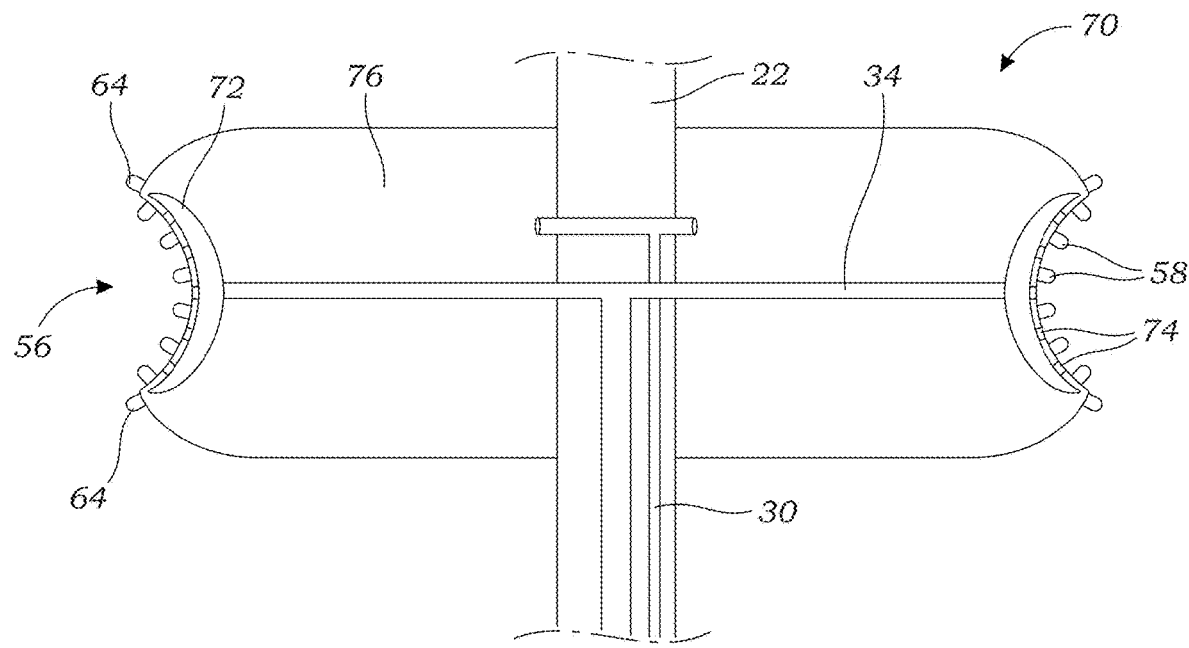
FIG. 8 is a side cross section of the gripping feature of FIG. 7, illustrating the gripping feature in an inflated state.

FIG. 7 is a side cross section of another embodiment of the gripping feature 70, illustrating the gripping feature 70 in a deflated state, and FIG. 8 is a side cross section of the gripping feature of FIG. 7, illustrating the gripping feature 70 in an inflated state. As shown in FIGS. 7-8, in this embodiment, the gripping feature 70 may include an inner body 72 that receives vacuum from the vacuum source 36 and which includes holes 74 formed in the clamping surface, while an outer body 76 receives pressure from the pressure source 32. In this embodiment, the spacers 62 of FIGS. 4-5 are not necessary for separating the inner and outer bodies to allow vacuum to pass therebetween. While FIG. 8 illustrates that the clamping surface may remain semi-concave in the inflated state, the arrangement of the inner and outer bodies 72 and 76 does not necessitate this, and it is intended only for the purpose of example. In this case, the side ridges 64 formed on outer edges of the clamping area 56 may also seal the area between the clamping area 56 and the luminal body 14 to contain the vacuum force.

Figure 9:
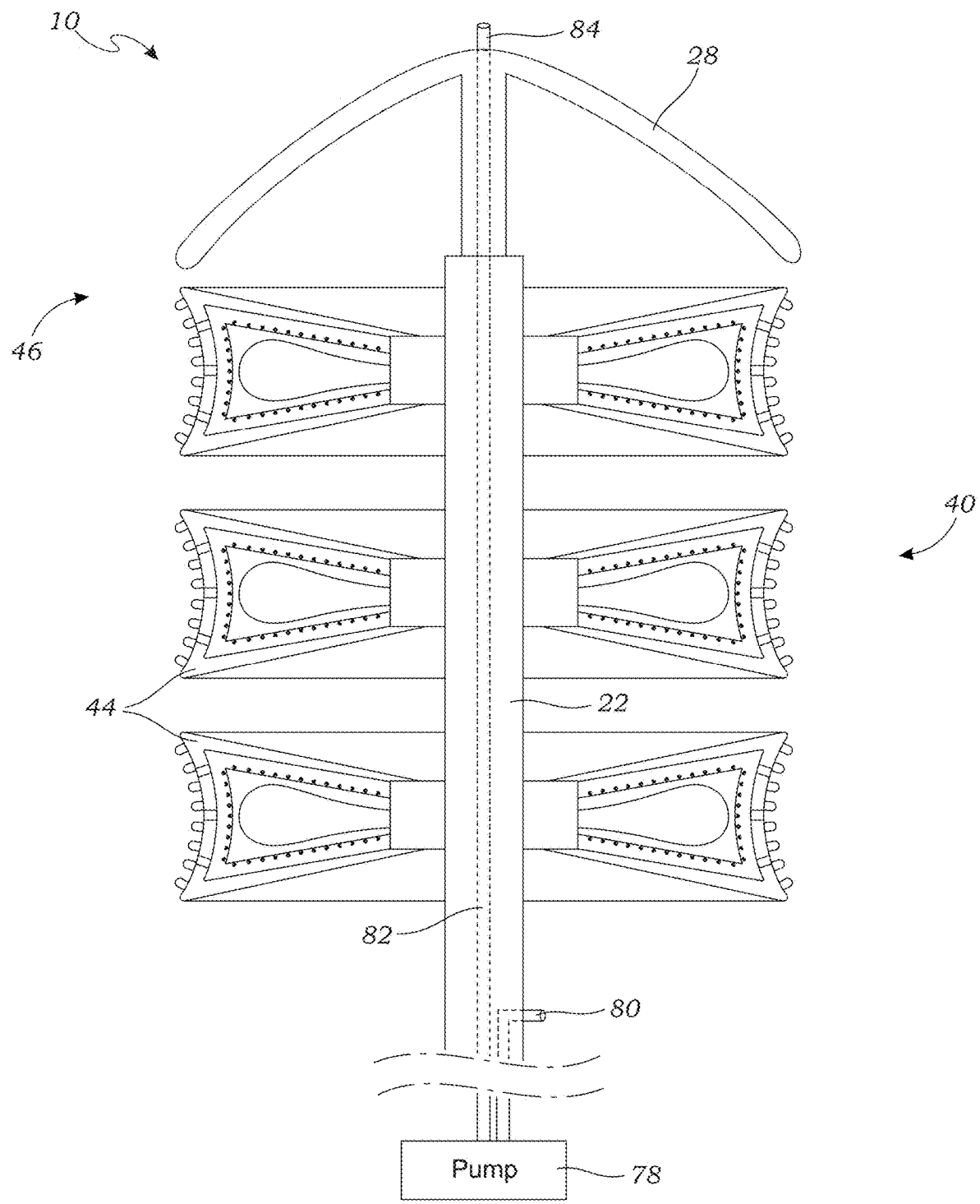
FIG. 9 is a side cross section of the gripping feature of FIG. 4, illustrating a fluid pump system integrated into the device.

FIG. 9 is a side cross section of the gripping feature 40 of FIG. 4, illustrating a fluid pump system 78 integrated into the device. As shown in FIG. 9, in this embodiment, the fluid pump system 78 may include an intake tube 80 (or port, hose, or other intake mechanism) that draws fluid from beneath the blocking device 20 and pumps it into a pump conduit 82 that extends from the proximal end 24 of the tubular body 22 and through to the distal end 26, to an outlet 84 of the guide cap 28. The fluid pump system 78 may be a hand pump, manual stroke, syringe, electric pump, etc., that pushes blood downstream to upstream. The pump 78 could be inside of the blocking device 20, or outside, depending on the needs of the medical professional.

If used with blood, the fluid pump system 78 functions to draw spilled blood present in the lower aorta or surrounding area, and pumps it into the upper aorta from where it can provide potentially vital support to the patient, who may be facing serious injury or death.

The title of the present application, and the claims presented, do not limit what may be claimed in the future, based upon and supported by the present application. Furthermore, any features shown in any of the drawings may be combined with any features from any other drawings to form an invention which may be claimed.

As used in this application, the words "a," "an," and "one" are defined to include one or more of the referenced item unless specifically stated otherwise. The terms "approximately" and "about" are defined to mean+/−10%, unless otherwise stated. Also, the terms "have," "include," "contain," and similar terms are defined to mean "comprising" unless specifically stated otherwise. Furthermore, the terminology used in the specification provided above is hereby defined to include similar and/or equivalent terms, and/or alternative embodiments that would be considered obvious to one skilled in the art given the teachings of the present patent application. While the invention has been described with reference to at least one particular embodiment, it is to be clearly understood that the invention is not limited to these embodiments, but rather the scope of the invention is defined by claims made to the invention.

What is claimed is:

1. A surgical system for blocking a luminal body at a selected location, the surgical system comprising:
a tubular body that extends from a proximal end to a distal end;
a blocking device on the distal end of the tubular body, the blocking device having a guide cap and a gripping feature;
at least one annular inflatable portion around an outer circumference of the gripping feature;
a first conduit through the tubular body connected to a pressure source for inflating the annular inflatable portion; and
further comprising a second conduit through the tubular body connected to a vacuum source for suctioning the luminal wall of the luminal body against the gripping feature.

2. The surgical system of claim 1, wherein the gripping feature includes at least one annular plug that extends radially from the tubular body and terminates in the inflatable portion.

3. The surgical system of claim 1, wherein the at least one inflatable portion includes an inner layer forming an inner body, and an outer layer having at least one hole and forming an outer body, and wherein the first conduit communicates with the inner body, and the second conduit communicates with the outer body, so that pressure may be applied to inflate the inner body, which presses the inflatable portion against the luminal body, and vacuum may be applied to the outer body to suction the inflatable portion to the luminal body.

4. The surgical system of claim 3, wherein a plurality of spacers on the outside of the inner layer maintains a separation between the inner and outer layers.

5. The surgical system of claim 1, further comprising a plurality of dividing walls extending radially from the tubular body within the inflatable portion, the dividing walls being circumferentially spaced to form a plurality of chambers in the inflatable portion.

6. The surgical system of claim 1, further comprising a pump having an intake tube that draws fluid from downstream of the blocking device and pumps it through a pump conduit and out of an outlet upstream of the blocking device.

7. A method for blocking a luminal body at a selected location, the method comprising the steps of:
    providing a blocking device having a tubular body that extends from a proximal end to a distal end, the distal end having a guide cap and at least one gripping feature, wherein each of the at least one gripping feature has an annular inflatable portion around an outer circumference of the gripping feature, and further comprising a second conduit through the tubular body to the inflatable portion;
    inserting the blocking device into the luminal body, and guiding it through the luminal body to the selected location;
    inflating the at least one annular inflatable portion of the gripping feature from a deflated state that is smaller than the diameter of the luminal body, to an inflated state that is large enough to frictionally engage the luminal body, thereby blocking the luminal body; and
    applying vacuum through the second conduit for suctioning the luminal wall of the luminal body against the gripping feature.

8. The method of claim 7, wherein the luminal body is an artery or vein.

9. The method of claim 7, further comprising the step of performing a surgical procedure on or near the luminal body.

* * * * *